United States Patent [19]

Whetstone

[11] 4,006,134
[45] Feb. 1, 1977

[54] CALCIUM SUGAR PHOSPHATES

[75] Inventor: John Whetstone, Woodlea, Scotland

[73] Assignee: Imperial Chemical Industries Limited, London, England

[22] Filed: Jan. 9, 1976

[21] Appl. No.: 647,981

Related U.S. Application Data

[60] Continuation of Ser. No. 392,488, Aug. 29, 1973, abandoned, which is a division of Ser. No. 177,980, Sept. 7, 1971, Pat. No. 3,782,901.

[30] Foreign Application Priority Data

Sept. 7, 1970 United Kingdom ............. 42763/70

[52] U.S. Cl. ............................... 536/117; 260/974; 23/252 R; 23/285
[51] Int. Cl.$^2$ ......................................... C08B 37/00
[58] Field of Search ............................... 260/234 R

[56] References Cited

UNITED STATES PATENTS 3,782,901  1/1974  Whetstone ..................... 260/234 R

*Primary Examiner*—Lewis Gotts
*Assistant Examiner*—Cary Owens
*Attorney, Agent, or Firm*—Cushman, Darby & Cushman

[57] ABSTRACT

Calcium sucrose phosphate is manufactured in a unit operating on a semi-continuous principle by circulating a lime-sugar slurry continuously at a high rate from a holding vessel through a heat exchanger as precooler, a cooled scraped-wall reactor into which phosphorus oxychloride is injected and then back to the holding vessel. The serious problem of gel formation of the reaction mixture on cooling surfaces is obviated by this circulation technique.

8 Claims, 1 Drawing Figure

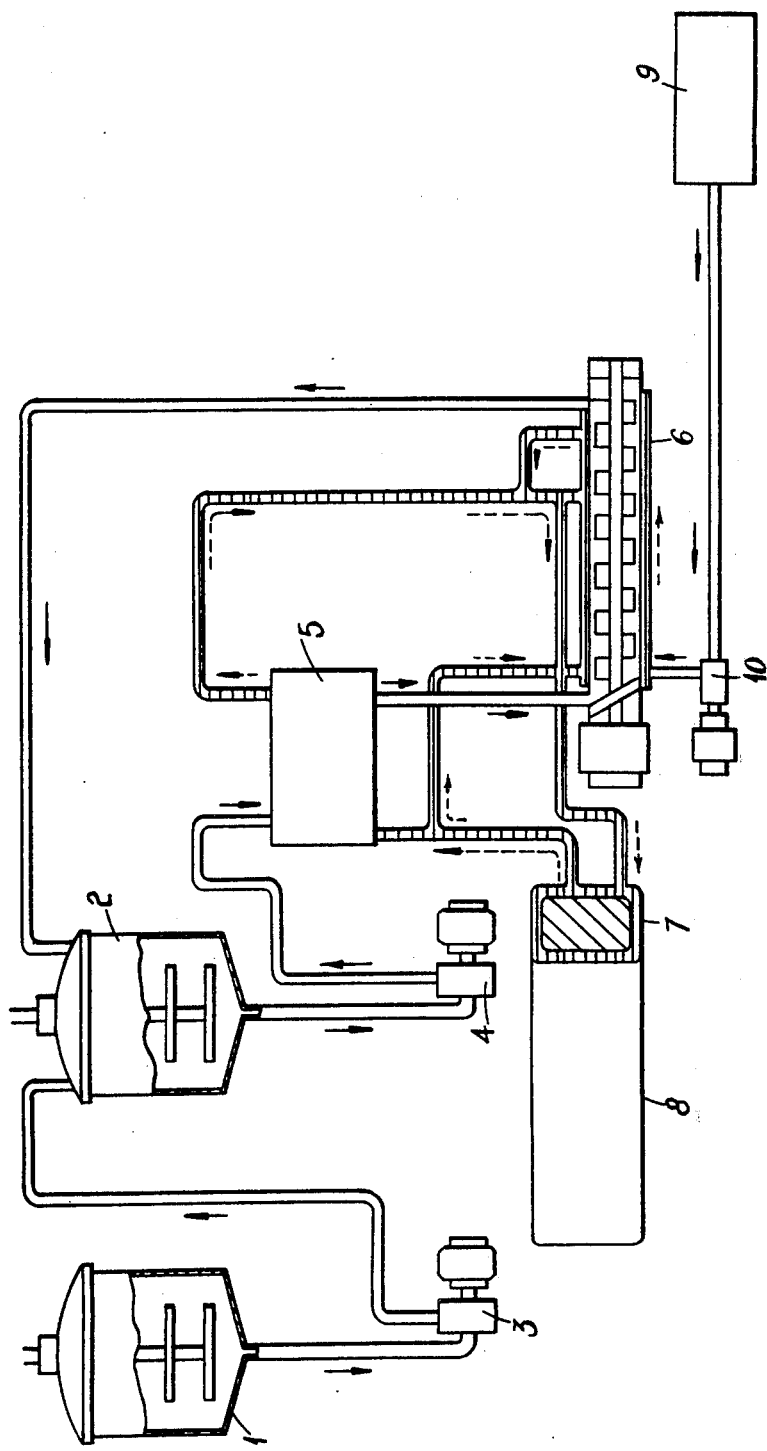

CALCIUM SUGAR PHOSPHATES

This application is a cont. of Ser. No. 392,488, filed Aug. 29, 1973, and now abandoned; which is a div. of Ser. No. 177,980, filed Sept. 7, 1971 now U.S. Pat. No. 3,782,901.

This invention relates to improvements in the manufacture of phosphoric esters of polyhydric alcohols.

More particularly, but not exclusively, the invention relates to improvements in the manufacture of calcium sugar phosphates.

Calcium sugar phosphates, and in particular calcium sucrose phosphate, are useful cariostatic agents and plant and animal nutrients.

Calcium sucrose phosphate is conveniently prepared by the phosphorylation of a sucrose solution in the presence of lime. German Pat. No. 247,809 describes the phosphorylation process as being carried out in an excess of lime whereas British Pat. No. 983,340 teaches that it is advantageous to employ stoichiometric quantities of the calcium oxy-compound. In both of these processes the phosphorylating agent ($POCL_3$) is added to the mixture in the presence of a chlorinated hydrocarbon.

British Pat. Nos. 1,115,370 and 1,134,062 specify the product as a complex association between the sugar phosphates and calcium phosphates and specific directions for obtaining an associated product of correct composition are quoted and these conditions are stated to be fairly critical in terms of raw material and product concentrations and the allowable temperature range of operation.

British Pat. No. 1,195,585 indicates that unexpectedly improved yields are obtained if the phosphorus oxychloride is added to the reaction mixture in the absence of the chlorinated hydrocarbon solvent which was previously thought to be necessary to prevent premature decomposition of the phosphorous oxychloride or the occurrence of undesirable side reactions. The last mentioned Patent Specification also indicates that clarification of the reaction mixture by centrifugation is advisable on completion of the reaction.

None of the above mentioned Patents, however, deals with a very serious problem which is experienced in the manufacture of calcium sucrose phosphate, namely the extremely high viscosities that can be obtained when lime reacts with sucrose in aqueous solution.

The reaction of calcium hydroxide, sucrose and phosphorus oxychloride to give calcium sucrose phosphate is exothermic and has a heat of reaction of 1,070 BTU/16 calcium sucrose phosphate. The limiting factor in the reaction time is, therefore, the rate at which heat can be removed as the reaction proceeds. In the temperature range 0° to 10° C, preferably 5° to 8° C, at which the conversion of sucrose to calcium sucrose phosphate is at a maximum, the heat removal is complicated by the aforesaid viscosity characteristics of the reaction mixture. The viscosity of a sucrose/lime slurry increases considerably as the temperature of the reaction mixture is reduced from 10° to 0° C and the slurry becomes viscous at 0° C and gels in time. On standing at higher temperatures the viscosity of the slurry also increases markedly with time. In this connection we have made the following specific observations.

a. The viscosity of the sucrose/lime slurry increases steadily with time to reach a maximum which is highest at low tempratures and below about 8° C the maximum is too high for effective stirring.

b. The faster the cooling to the preferred reaction temperature of 5° C is performed, the lower is the resulting viscosity of the slurry.

c. In the early stages of phosphorous oxychloride addition, viscosity is influenced by two factors:
  i. the tendency for increase in the length of the polymeric chains of the calcium sucrate formed by the reaction between the lime and sucrose with consequent increase in viscosity, and
  ii. the break-up of the polymeric chains and reduction in viscosity on reaction with phosphorous oxychloride.

If the rate of addition of phosphorous oxychloride is slow, some time elapses before factor (ii) becomes predominant. Fast addition of phosphorous oxychloride results in an immediate and continuous drop in viscosity.

d. When phosphorous oxychloride addition is stopped after one fifth of the total amount required for reaction has been added and the mixture held at 5° C, no viscosity increase with time is observed.

As a result of the above observations we have determined that the viscosity problems in the production of calcium sucrose phosphate can, therefore, be minimised to a certain extent by:

1. cooling the sucrose/lime slurry rapidly to the preferred reaction temperature of 5° C, and
2. adding phosphorous oxychloride as fast as possible initially, consistent with maintaining the low temperature, to prevent a continued build-up of viscosity.

More important, however, we have determined that the most important factor in obtaining an efficient and economical process for the manufacture of calcium sucrose phosphate is tied up with the design of the plant employed. From the above discussion it will be realised that the gelling of the sucrose/lime slurry at below 10° C, and with time, imposes a serious limitation on the ease of removal by cooling of the 1070 BTU/16 heat of reaction in the forming of the calcium sucrose phosphate. Owing to the danger of forming a gelled layer on cooled surfaces, it has hitherto been impossible to remove this heat of reaction rapidly by using a coolant at such a temperature as to remove the heat at the desired rate at the optimum temperature range of 0°–10° C. The high viscosity of the mixture in the early stages tends to prevent the stirring action of the stirrer from extending all over the reactor and the material in the area of the reactor walls remains relatively static, thus aiding the formation of gelled layers and slowing down the heat transfer in stirred reactors with cooling jackets. Scaling up from laboratory scale to industrial plant becomes a problem because of the decreasing ratio of cooling surface area to volume as the capacity of the reactor is increased and the small permissible temperature gradient between the contents of the reactor and the coolant if the process is operated within the optimum temperature range of 0°–10° C.

The most obvious effect of scaling up the process in stirred reactors is the increase of time which is required to dissipate the heat of reaction with the small permissible temperature gradient. This can be illustrated with reference to glass reaction flasks of 500 ml, 20 l. and 100 l. size. In cooling baths giving temperatures of 5°–7° C, the reaction times were found to be ¾, 3 and 11 hours respectively. These results indicate that stirring in a batch reactor is extremely inefficient. It is obvious that further scaling up to an industrial scale presents difficulties in view of the geometrical factor of the cooling surface area/volume ratio.

It is an object of the present invention, therefore, to provide a means of overcoming and eliminating the aforesaid viscosity problem in the manufacture of calcium sucrose phosphate.

Whilst the subject invention was developed as a means of overcoming this viscosity problem which is peculiar to the manufacture of calcium sucrose phosphate, it is to be understood that the subject invention can also be applied to the manufacture of other phosphoric esters of polyhydric alcohols. A further object of the invention, therefore, is to provide a means of manufacturing phosphoric esters of polyhydric alcohols which is economically superior to the manufacturing techniques described in the prior art.

According to the present invention there is provided a process for the manufacture of a phosphoric acid ester of a polyhydric alcohol comprising continuously circulating an aqueous solution or slurry of a polyhydric alcohol and an inorganic calcium oxy-compound around a closed reaction system, cooling said circulating solution or slurry to an optimum temperature for phosphorylation and phosphorylating said cooled solution or slurry in a cooled stirred reaction zone of the closed system.

Preferably, said slurry is pumped around said reaction system at a rate sufficient to prevent gelling on the surfaces thereof.

Further preferably, the stirring action in the reaction zone is such as to ensure continuous scraping of any gelled slurry from the surfaces of the reaction zone.

The polyhydric alcohol is preferably a sugar selected from sucrose, galactose, arabinose, ribose, xylose, maltose, lactose, raffinose or glucose.

The polyhydric alcohol may be mannitol, sorbitol or glycerol. The calcium oxy-compound is preferably calcium oxide, calcium hydroxide or calcium carbonate and the phosphorylating agent is preferably phosphorous oxychloride.

The present invention is also a continuous flow reaction system for the manufacture of a phosphoric acid ester of a polyhydric alcohol by the phosphorylation of an aqueous solution or slurry of the alcohol and an inorganic calcium oxy-compound comprising a holding vessel for said aqueous slurry, a continuous flow scraped-wall reactor adapted to receive slurry from and deliver slurry to said holding vessel, refrigeration means for continuously cooling slurry to an optimum reaction temperature prior to its entry into the reactor and for continuously maintaining the reactor contents at said optimum temperature during the phosphorylation reaction, first pumping means for circulating slurry continuously around the reaction system and second pumping means for supplying phosphorylating agent to the reactor.

In this Specification the term scraped-wall reactor is to be understood as meaning a reactor provided with stirring means adapted for continuous scraping of any gelled slurry from the surface of the reactor.

Preferably, the slurry is cooled to the reaction temperature in a heat exchanger connected in series with the scraped-wall reactor.

Further preferably, said refrigeration means is adapted to circulate coolant fluid through the heat exchanger and a cooling jacket of the scraped-wall reactor.

The present invention is also a phosphoric acid ester of a polyhydric alcohol whenever prepared by the above described process or obtained from the above continuous flow reaction system.

An embodiment of the invention will now be described, simply by way of example, with reference to the accompanying drawing which illustrates a preferred form of a continuous flow reaction system for the manufacture of calcium sucrose phosphate.

We have discovered that in scaling up the calcium sucrose phosphate process to industrial proportions, the limiting geometrical factor of the cooling surface area/volume ratio can be avoided by extending the reaction vessel by means of pumping its contents through a continuous flow reaction system or circulation ring main embodying an efficient heat exchanger in series with a scraped-wall stirred tubular reactor. A suitable type of reactor is a scraped-wall tubular crystalliser. The effective mixing of the immiscible phosphorous oxychloride and aqueous phases, and hence their rate of reaction, is partly controlled by the speed at which the wall-scraping stirrer is operated.

The heat exchanger and scraped-wall crystalliser are cooled by an efficient circulation of refrigerant and it is unnecessary to cool the slurry holding vessel directly.

It is thus possible to manufacture calcium sucrose phosphate with a much improved efficiency by taking advantage of the continuously scraped cooling surfaces in the scraped-wall reactor, which effectively prevents any building up of gelled material on the cooling surface and allows very efficient cooling of the contents of the reactor and, moreover, as aforesaid, the rotating action of the scraper blades provides thorough mixing of the contents. The phosphorous oxychloride is pumped through a metering pump into the reactor at the point of entry of the slurry and the heat is efficiently removed on the scraped-wall surfaces by the refrigerant. By controlling the flow rate of phosphorous oxychloride into the reactor, it is possible to vary the temperature at which the reaction is carried out.

Referring to the drawing, a sucrose solution is made up in stirred vessel 1 and a lime slurry in stirred vessel 2. In this preferred embodiment no refrigeration is applied to vessels 1 or 2. The sucrose solution is pumped by pump 3 into vessel 2 which is efficiently stirred and constitutes the holding vessel of the continuous flow reaction system. The slurry in vessel 2 comprises 1 part sucrose, 0.57 part lime and 2.84 parts water. Heat is evolved on the mixing of the two solutions in vessel 2, causing a temperature rise of approximately 6.5° C. This heat of reaction is dissipated as quickly as possible by circulating the slurry in holding vessel 2 via a pump 4 into a heat exchanger 5 and a scraped-wall reactor 6, through the cooling jackets of which an ethylene glycol/water solution at 0° C is pumped by pump 7 which is in series with a refrigerating machine 8. The sucrose/lime slurry is pumped for approximately three-quarters of an hour around the system, during which time the contents of the vessel 2 are reduced to 7° C. At this point the injection of phosphorus oxychloride from a storage vessel 9 through metering pump 10 into the stream of sucrose/lime slurry being fed into the reactor 6 is started. The slurry at 7° C leaving the holding vessel 2 is cooled by means of heat exchanger 5 to a temperature of 5° C prior to entering the reactor 6. The circulating slurry leaves the reactor at a temperature of 7° C. Pumping of phosphorous oxychloride is continued at such a rate that the material leaving the reactor 6 and passing to the holding vessel 2 does not rise above 7° C. The blades of the reactor are on a shaft rotating at 30–60 rpm. In a modified system, the slurry entering the reactor 6 from heat exchanger 5 is at a temperature of 3°–4° C and after leaving the reactor its temperature is 6° C.

By means of the continuous flow reaction system of the invention it was found that 300 gallons of the aqueous sucrose/lime slurry could be processed in under 8 hours and that the temperature control effectively improved the product. The residence time of the material in the reactor during each pass is approximately 30 seconds, sufficient for the phosphorous oxychloride to have completely reacted. The phosphorylating reaction was deemed to be complete when the circulating slurry had attained a pH of 8–9. A suitable rate of slurry circulation was found to be 1500 gallons/hour.

After centrifuging off the suspended material in a Sharples centrifuge, the solution of calcium sucrose phosphate produced was water-white instead of discoloured brown as produced in the batch-type reactions in the stirred vessels of the prior art. When isolated by precipitation with alcohol or other such means (e.g. spray-drying), the calcium sucrose phosphate produced by the system of the invention was snow-white in colour and not tinted yellow or buff colour.

Possible modifications of the preferred system are as follows:

1. A special reactor could be designed which includes a heat exchanger as an integral part of the reactor, or alternatively the cooling surface of the reactor could be increased to such an extent that a separate heat exchanger is unnecessary.

2. The batch process constituting the preferred embodiment could be modified very simply for continuous production. The continuous process would be run similar to the batch process until the desired pH value is attained and fresh sugar/lime slurry would then be supplied to the holding vessel at a rate commensurate with the rate at which reaction product is drawn off.

3. The sugar solution and lime slurry could be cooled separately before mixing in the holding vessel but there would still be a rise in temperature of about 6° C when they are brought together, so cooling of the combined slurry in the ring main would still be required.

What I claim is:

1. In a process for the manufacture of a phosphoric acid ester of a polyhydric alcohol by cooling an aqueous solution or slurry of a polyhydric alcohol and an inorganic calcium oxy-compound to a temperature between 0° and 10° C. and then phosphorylating the cooled solution or slurry with phosphorous oxychloride, the improvement comprising circulating the solution or slurry around a closed loop reaction system which includes a cooling zone and a cooled and stirred reaction zone, cooling said circulating solution or slurry by circulation through the cooling zone to reduce the temperature thereof to near 10° C., then further cooling said circulating solution or slurry to a temperature of 0° C to 10° C and then phosphorylating said further cooled solution or slurry with the said phosphorous oxychloride in the cooled and stirred reaction zone.

2. A process as claimed in claim 1 wherein said slurry is pumped around said reaction system at a rate sufficient to prevent gelling on the surfaces thereof.

3. A process as claimed in claim 1 wherein the stirring action in the reaction zone is such as to ensure continuous scraping of any gelled slurry from the surfaces of the reaction zone.

4. A process as claimed in claim 1 wherein the polyhydric alcohol is a sugar.

5. A process as claimed in claim 4 wherein the sugar is sucrose, galactose, arabinose, ribose, xylose, maltose, lactose, raffinose or glucose.

6. A process as claimed in claim 1 wherein the polyhydric alcohol is mannitol, sorbitol or glycerol.

7. A process as claimed in claim 1 wherein the inorganic calcium oxy-compound comprises calcium oxide, calcium hydroxide or calcium carbonate.

8. A continuous flow reaction system for the manufacture of a phosphoric acid ester of a polyhydric alcohol by the phosphorylation of an aqueous solution or slurry of the alcohol and an inorganic calcium oxy-compound comprising a holding vessel for said aqueous slurry, a continuous flow scraped-wall reactor adapted to receive slurry from and deliver slurry to said holding vessel, refrigeration means for continuously cooling slurry to an optimum reaction temperature prior to its entry into the reactor and for continuously maintaining the reactor contents at said optimum temperature during the phosphorylation reaction, first pumping means for circulating slurry continuously around the reaction system and second pumping means for supplying phosphorylating agent to the reactor.

* * * * *